US009550066B2

(12) United States Patent
An et al.

(10) Patent No.: US 9,550,066 B2
(45) Date of Patent: *Jan. 24, 2017

(54) SYSTEM AND METHODS FOR IMPROVING DEVICE THERAPY USING MULTIPLE SENSOR METRICS

(71) Applicant: Cardiac Pacemakers, Inc., St. Paul, MN (US)

(72) Inventors: Qi An, Blaine, MN (US); Barun Maskara, Blaine, MN (US); Pramodsingh Hirasingh Thakur, Woodbury, MN (US); Julie A. Thompson, Circle Pines, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/969,638

(22) Filed: Dec. 15, 2015

(65) Prior Publication Data

US 2016/0101290 A1  Apr. 14, 2016

Related U.S. Application Data

(63) Continuation of application No. 14/199,651, filed on Mar. 6, 2014, now Pat. No. 9,254,390.

(Continued)

(51) Int. Cl.
*A61N 1/368* (2006.01)
*A61N 1/362* (2006.01)
(Continued)

(52) U.S. Cl.
CPC ........... *A61N 1/36585* (2013.01); *A61N 1/056* (2013.01); *A61N 1/365* (2013.01); *A61N 1/368* (2013.01);
(Continued)

(58) Field of Classification Search
CPC ...... A61N 1/365; A61N 1/368; A61N 1/3627; A61N 1/3704; A61B 1/056
(Continued)

(56) References Cited

U.S. PATENT DOCUMENTS 7,079,896 B1  7/2006  Park et al.
8,041,424 B2  10/2011  Corbucci
(Continued)

FOREIGN PATENT DOCUMENTS

WO  WO-2014158986 A1  10/2014

OTHER PUBLICATIONS

"U.S. Appl. No. 14/199,651, Non Final Office Action mailed Apr. 21, 2015", 13 pgs.
(Continued)

*Primary Examiner* — Carl H Layno
*Assistant Examiner* — Jon Eric C Morales
(74) *Attorney, Agent, or Firm* — Schwegman Lundberg & Woessner, P.A.

(57) ABSTRACT

Devices and methods for improving device therapy such as cardiac resynchronization therapy (CRT) by determining a desired value for a device parameter are described. An ambulatory medical device can receive one or more physiologic signals and generate multiple signal metrics from the physiologic signals. The ambulatory medical device can determine a desired value for a device parameter, such as a timing parameter used for controlling the delivery of CRT pacing to various heart chambers, using information fusion of signal metrics that are selected based on one or more of a signal metric sensitivity to perturbations to the device parameter in response to a stimulation, a signal metric variability in response to a stimulation, or a covariability between two or more signal metrics in response to a stimulation. The ambulatory medical device can program a stimu-
(Continued)

lation using the desired device parameter value, and deliver the programmed stimulation to one or more target sites to achieve desired therapeutic effects.

20 Claims, 6 Drawing Sheets

Related U.S. Application Data

(60) Provisional application No. 61/776,893, filed on Mar. 12, 2013.

(51) Int. Cl.
    *A61N 1/365*      (2006.01)
    *A61N 1/05*      (2006.01)
    *A61N 1/36*      (2006.01)
    *A61N 1/37*      (2006.01)

(52) U.S. Cl.
    CPC ........... *A61N 1/3625* (2013.01); *A61N 1/3627* (2013.01); *A61N 1/3682* (2013.01); *A61N 1/3684* (2013.01); *A61N 1/36139* (2013.01); *A61N 1/36514* (2013.01); *A61N 1/3704* (2013.01)

(58) Field of Classification Search
    USPC ....................... 600/484–485, 528; 607/17–18
    See application file for complete search history.

(56) References Cited

U.S. PATENT DOCUMENTS

| | | |
|---|---|---|
| 8,060,201 B2 | 11/2011 | Holmström et al. |
| 8,229,557 B2 | 7/2012 | Patangay et al. |
| 2004/0220636 A1 | 11/2004 | Burnes |
| 2007/0093873 A1 | 4/2007 | Chirife et al. |
| 2009/0082823 A1 | 3/2009 | Shuros et al. |
| 2010/0113890 A1 | 5/2010 | Cho et al. |
| 2010/0152796 A1 | 6/2010 | Schecter |
| 2010/0274141 A1 | 10/2010 | Patangay et al. |
| 2011/0125208 A1 | 5/2011 | Karst et al. |
| 2014/0277235 A1 | 9/2014 | An et al. |

OTHER PUBLICATIONS

"U.S. Appl. No. 14/199,651, Notice of Allowance mailed Oct. 6, 2015", 8 pgs.

"U.S. Appl. No. 14/199,651, Response filed Jul. 21, 2015 to Non Final Office Action mailed Apr. 21, 2015", 15 pgs.

"International Application Serial No. PCT/US2014/021287, International Preliminary Report on Patentability mailed Sep. 24, 2015", 9 pgs.

"International Application Serial No. PCT/US2014/021287, International Search Report mailed May 26, 2014", 5 pgs.

"International Application Serial No. PCT/US2014/021287, Written Opinion mailed May 26, 2014", 7 pgs.

SYSTEM AND METHODS FOR IMPROVING DEVICE THERAPY USING MULTIPLE SENSOR METRICS

CLAIM OF PRIORITY

This application is a continuation of U.S. application Ser. No. 14/199,651, filed Mar. 6, 2014, now issued as U.S. Pat. No. 9,254,390, which claims the benefit of priority under 35 U.S.C. §119(e) of U.S. Provisional Patent Application Ser. No. 61/776,893, filed on Mar. 12, 2013, each of which is herein incorporated by reference in its entirety.

TECHNICAL FIELD

This document relates generally to medical devices, and more particularly, to systems, devices and methods for improving a device therapy using multiple sensor metrics.

BACKGROUND

Congestive heart failure (CHF) is a major health problem and affects over five million people in the United States alone. CHF is the loss of pumping power of the heart, resulting in the inability to deliver enough blood to meet the demands of peripheral tissues. CHF patients typically have enlarged heart with weakened cardiac muscles, resulting in reduced contractility and poor cardiac output of blood.

CHF is usually a chronic condition, but can occur suddenly. It can affect the left heart, right heart or both sides of the heart. If CHF affects the left ventricle, signals that control the left ventricular contraction are delayed, and the left and right ventricles do not contract simultaneously. Non-simultaneous contractions of the left and right ventricles further decrease the pumping efficiency of the heart.

SUMMARY

CHF can be treated by cardiac pacing therapy. Pacing therapy to promote synchronization of heart chamber contractions for improved cardiac function is generally referred to as cardiac resynchronization therapy (CRT). Ambulatory medical devices such as cardiac pacemakers are capable of delivering CRT by pacing multiple heart chambers. Some ambulatory medical devices can pace the heart chambers in a sequence that causes the heart chambers to contract in synchrony, thereby increasing the pumping power of the heart and delivering more blood to the peripheral tissues of the body. In the case of dyssynchrony of right and left ventricular contractions, a biventricular pacing therapy can be used to resynchronize the left and right ventricles. Bi-atrial pacing or pacing of all four heart chambers can also be used.

Improving the CRT therapy by determining desired CRT parameters involves determining desired pacing parameters, such as intervals between pacing pulses delivered to various heart chambers that provide effective CRT delivery. Due to the variation across patient population in their responses to CRT as well as the within patient variation in optimal CRT setting as a result of, for example, changes in the patient's activity level, disease progression, medication, and general health condition, the patient response to CRT vary; and the therapy parameter need to be timely adjusted to provide and maintain desired cardiac function to the patient. The present inventors have recognized that there remains a considerable need of devices and methods that can automatically improve the device therapy by properly setting the CRT parameters on an individualized basis.

Various examples described herein can help improve the process of improving the device therapy such as cardiac resynchronization therapy (CRT). For example, an ambulatory medical device can receive one or more physiologic signals such as from a physiologic sensor and generate two or more signal metrics from the physiologic signals. The ambulatory medical device can include a device parameter adjustment circuit configured to determine a desired value for a device parameter, such as a timing parameter which can be used to control the delivery of CRT pacing to various heart chambers using information fusion. The device parameter adjustment circuit can include one or more of a sensitivity calculator circuit, a variability calculator circuit, or a covariability calculator circuit. The sensitivity calculator circuit can be configured to determine for at least two of the two or more signal metrics a respective sensitivity to a perturbation to the device parameter in response to stimulations. The variability calculator circuit can be configured to determine for at least two of the two or more signal metrics a respective variability in response to the stimulations. The covariability calculator circuit can be configured to determine a covariability between at least two of the two or more signal metrics in response to the stimulations. An information fusion circuit can determine the desired device parameter value using one or more of the sensitivity, the variability, or the covariability. A controller circuit can program stimulations using the desired device parameter value, and a stimulation generation circuit can generate the programmed stimulations and deliver the stimulations to one or more target sites.

A method can include sensing one or more physiologic signals and generating two or more signal metrics from the physiologic signals. The method can include calculating a sensitivity of the signal metrics in response to stimulation with a perturbation to the device parameter, a variability of the signal metrics in response to the stimulation with a specified device parameter, and a covariability between two or more signal metrics in response to the stimulation with a specified device parameter. The method can then use one or more of the sensitivity, the variability, or the covariability to determine a desired value for the device parameter, such as a timing parameter which can be used to control the delivery of CRT pacing to various heart chambers. The method includes generating stimulations according to the desired value for the device parameter and delivering the stimulations the target sites.

Another method can include sensing one or more physiologic signals and generating two or more signal metrics from the physiologic signals, and determine a target directional vector using the difference between a first signal metric vector in response to stimulation when the device parameter is set to a first value, and a second signal metric vector in response to stimulation when the device parameter is set to a second value. Each signal metric vector comprises values of the two or more signal metrics measured during the respective stimulation. One of the first value or the second value of the device parameter includes a sub-optimal value. The method can construct a test signal metric vector in response to stimulation when the device parameter is set to a candidate value, and compute a projection of the test signal metric vector onto the target directional vector. When the projection meets a convergence criterion, the candidate value is determined to be a desired device parameter value.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices and methods for improving a device therapy using multiple sensor metrics. The device therapy can include cardiac pacing therapy provided by an implantable medical device such as a pacemaker, an implantable cardioverter-defibrillator (ICD), or a cardiac resynchronization therapy (CRT) device. The improvement of the cardiac pacing therapy can include determining a desired value for a relative timing between a first event in a heart chamber and a second event in a different heart chamber, such as intervals between pacing pulses delivered to atria and ventricles that provide effective CRT delivery. The present document discussed methods and devices for improving the device parameters using multiple sensor metrics and information fusion. The methods and devices described herein can also be applicable to improving other device functions pertaining to an implantable medical device, including such as pacing therapy, defibrillation therapy, neural stimulation therapy, and patient diagnostics and stratifying a patient's risk of developing a disease or a condition, or to monitoring a patient's health status or response to a medical intervention.

Figure 1:
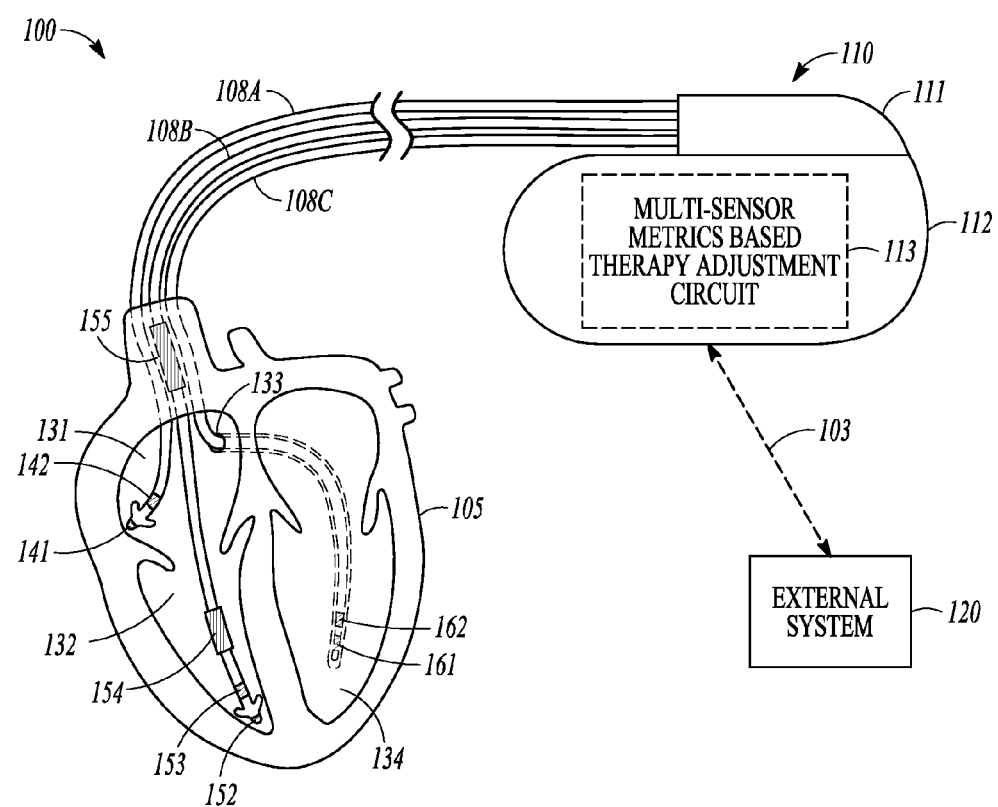
FIG. 1 illustrates an example of cardiac rhythm management (CRM) system and portions of the environment in which the CRM system operates.

FIG. 1 illustrates an example of a Cardiac Rhythm Management (CRM) system 100 and portions of an environment in which the CRM system 100 can operate. The CRM system 100 can include an ambulatory medical device, such as an implantable medical device (IMD) 110 that can be electrically coupled to a heart 105 such as through one or more leads 108A-C, and an external system 120 that can communicate with the IMD 110 such as via a communication link 103. The IMD 110 can include an implantable cardiac device such as a pacemaker, an implantable cardioverter-defibrillator (ICD), or a cardiac resynchronization therapy (CRT) device. The IMD 110 can include one or more monitoring or therapeutic devices such as a subcutaneously implanted device, a wearable external device, a neural stimulator, a drug delivery device, a biological therapy device, or one or more other ambulatory medical devices. The IMD 110 can be coupled to, or can be substituted by a monitoring medical device such as a bedside or other external monitor.

As illustrated in FIG. 1, the IMD 110 can include a hermetically sealed can 112 that can house an electronic circuit that can sense a physiologic signal in the heart 105 and can deliver one or more therapeutic electrical stimulations to a target region, such as in the heart, such as through one or more leads 108A-C. The CRM system 100 can include only one lead such as 108B, or can include two leads such as 108A and 108B.

The lead 108A can include a proximal end that can be configured to be connected to IMD 110 and a distal end that can be configured to be placed at a target location such as in the right atrium (RA) 131 of the heart 105. The lead 108A can have a first pacing-sensing electrode 141 that can be located at or near its distal end, and a second pacing-sensing electrode 142 that can be located at or near the electrode 141. The electrodes 141 and 142 can be electrically connected to the IMD 110 such as via separate conductors in the lead 108A, such as to allow for sensing of the right atrial activity and optional delivery of atrial pacing pulses. The lead 108B can be a defibrillation lead that can include a proximal end that can be connected to IMD 110 and a distal end that can be placed at a target location such as in the right ventricle (RV) 132 of heart 105. The lead 108B can have a first pacing-sensing electrode 152 that can be located at distal end, a second pacing-sensing electrode 153 that can be located near the electrode 152, a first defibrillation coil electrode 154 that can be located near the electrode 153, and a second defibrillation coil electrode 155 that can be located at a distance from the distal end such as for superior vena cava (SVC) placement. The electrodes 152 through 155 can be electrically connected to the IMD 110 such as via separate conductors in the lead 108B. The electrodes 152 and 153 can allow for sensing of a ventricular electrogram (EGM) and can optionally allow delivery of one or more ventricular pacing pulses, and electrodes 154 and 155 can allow for delivery of one or more ventricular cardioversion/defibrillation pulses. In an example, the lead 108B can include only three electrodes 152, 154 and 155. The electrodes 152 and 154 can be used for sensing or delivery of one or more ventricular pacing pulses, and the electrodes 154 and 155 can be used for delivery of one or more ventricular cardioversion or defibrillation pulses. The lead 108C can include a proximal end that can be connected to the IMB 110 and a distal end that can be configured to be placed at a target location such as in a left ventricle (LV) 134 of the heart 105. The lead 108C can be implanted through the coronary sinus 133 and can be placed in a coronary vein over the LV such as to allow for delivery of one or more pacing pulses to the LV. The lead 108C can include an electrode 161 that can be located at a distal end of the lead 108C and another electrode 162 that can be located near the electrode 161. The electrodes 161 and 162 can be electrically connected to the IMB 110 such as via separate conductors in the lead 108C such as to allow for sensing of the LV EGM and optionally allow delivery of one or more resynchronization pacing pulses from the LV.

The IMD 110 can include an electronic circuit that can sense a physiologic signal. The physiologic signal can include a EGM or a signal representing mechanical function of the heart 105. The hermetically sealed can 112 can function as an electrode such as for sensing or pulse delivery. For example, an electrode from one or more of the leads 108A-C can be used together with the can 112 such as for unipolar sensing of a EGM or for delivering one or more pacing pulses. A defibrillation electrode from the lead 108B can be used together with the can 112 such as for delivering one or more cardioversion/defibrillation pulses. In an example, the IMB 110 can sense impedance such as between electrodes located on one or more of the leads 108A-C or the can 112. The IMB 110 can be configured to inject current between a pair of electrodes, sense the resultant voltage between the same or different pair of electrodes, and determine impedance using Ohm's Law. The impedance can be sensed in a bipolar configuration in which the same pair of electrodes can be used for injecting current and sensing voltage, a tripolar configuration in which the pair of electrodes for current injection and the pair of electrodes for voltage sensing can share a common electrode, or tetrapolar configuration in which the electrodes used for current injection can be distinct from the electrodes used for voltage sensing. In an example, the IMB 110 can be configured to inject current between an electrode on the RV lead 108B and the can housing 112, and to sense the resultant voltage between the same electrodes or between a different electrode on the RV lead 108B and the can housing 112. A physiologic signal can be sensed from one or more physiological sensors that can be integrated within the IMD 110. The IMB 110 can also be configured to sense a physiologic signal from one or more external physiologic sensors or one or more external electrodes coupled to the IMB 110. Examples of the physiologic signal can include one or more of intrathoracic impedance, intracardiac impedance, arterial pressure, pulmonary artery pressure, RV pressure, LV coronary pressure, coronary blood temperature, blood oxygen saturation, one or more heart sounds, physical activity or exertion level, posture, respiration, body weight, or body temperature.

The arrangement and functions of these leads and electrodes are described above by way of example and not by way of limitation. Depending on the need of the patient and the capability of the implantable device, other arrangements and uses of these leads and electrodes are possible.

As illustrated, the CRM system 100 can include a multi-sensor metrics based therapy adjustment circuit 113. The multi-sensor metrics based therapy adjustment circuit 113 can be configured to improve the therapy such as determining desired values for device parameters used for sensing a physiologic event, providing patient diagnostic information, assessing device operation and functionality, or controlling the generation and delivery of device therapy such as stimulations to the patient. One example of device parameter includes timing of the delivery of pacing pulses to the heart such as an atrial-ventricular delay (AVD). The AVD represents the latency between an intrinsically occurred atrial electrical activation signal (As) such as sensed by the electrodes on the lead 108A and a subsequent ventricular pacing pulse (Vp) such as delivered through the electrodes on the lead 108B, or between an atrial pacing pulse (Ap) such as delivered through the electrodes on lead 108A and the subsequent Vp. In another example, the device parameter includes a left ventricular-right ventricular delay (VVD) which represents the latency between a left ventricular pacing pulse (LVp) such as delivered through the electrodes on the lead 108C a right ventricular pacing pulse (RVp) such as delivered through the electrodes on the lead 108B. In determining a desired value for a device parameter, the multi-sensor metrics based therapy adjustment circuit 113 can be coupled to one or more physiologic sensors or sensing electrodes such as the electrodes on one or more of the leads 108A-C and receive physiologic signals from the physiologic sensors or electrodes. In an example, the IMD 110 can program the stimulations (such as atrial pacing pulses, ventricular pacing pulses, cardioversion pulses, defibrillation pulses, or neural stimulations) and schedule the delivering of the stimulations using the desired device parameter value. Examples of the multi-sensor metrics based therapy adjustment circuit 113 are discussed below, such as with reference to FIGS. 2-4.

The external system 120 can allow for programming of the IMB 110 and can receives information about one or more signals acquired by IMB 110, such as can be received via a communication link 103. The external system 120 can include a local external IMD programmer. The external system 120 can include a remote patient management system that can monitor patient status or adjust one or more therapies such as from a remote location.

The communication link 103 can include one or more of an inductive telemetry link, a radio-frequency telemetry link, or a telecommunication link, such as an internet connection. The communication link 103 can provide for data transmission between the IMD 110 and the external system 120. The transmitted data can include, for example, real-time physiological data acquired by the IMD 110, physiological data acquired by and stored in the IMD 110, therapy history data or data indicating IMB operational status stored in the IMD 110, one or more programming instructions to the IMB 110 such as to configure the IMB 110 to perform one or more actions that can include physiological data acquisition such as using programmably specifiable sensing electrodes and configuration, device self-diagnostic test, or delivery of one or more therapies.

The multi-sensor metrics based therapy adjustment circuit 113 can be implemented at the external system 120, which can be configured to perform target event detection such as using data extracted from the IMD 110 or data stored in a memory within the external system 120. Portions of the multi-sensor metrics based therapy adjustment circuit 113 can be distributed between the IMB 110 and the external system 120.

Portions of the IMD 110 or the external system 120 can be implemented using hardware, software, or any combination of hardware and software. Portions of the IMB 110 or the external system 120 can be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals.

Figure 2:
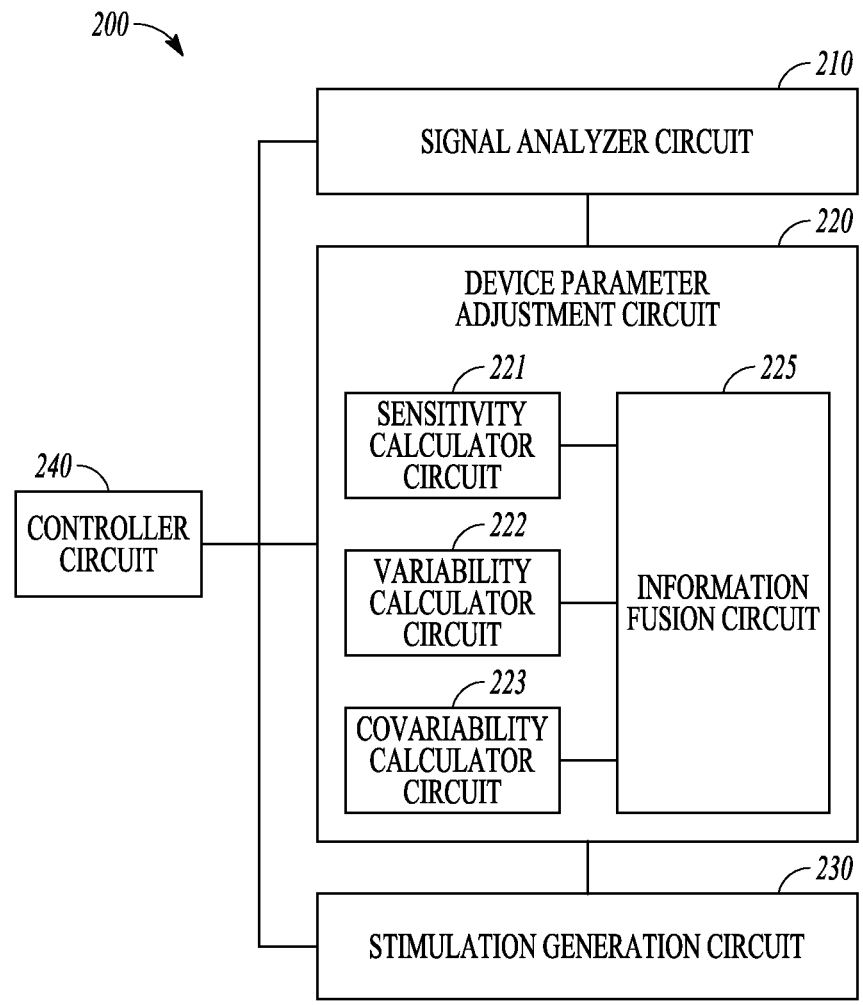
FIG. 2 illustrates an example of a device therapy adjustment circuit.

FIG. 2 illustrates an example of a device therapy adjustment circuit 200, which can be an example of the multi-sensor metrics based therapy adjustment circuit 113. The device therapy adjustment circuit 200 can include a signal analyzer circuit 210, a device parameter adjustment circuit 220, a stimulation generation circuit 230, and a controller circuit 240.

The signal analyzer circuit 210 can receive one or more physiologic signals and generate two or more signal metrics from the physiologic signals. Examples of the physiologic signal can include EGM from the electrodes on leads 108A-C and the can 112, intrathoracic impedance, intracardiac impedance, arterial pressure, pulmonary artery pressure, RV pressure, LV coronary pressure, coronary blood temperature, blood oxygen saturation, heart sounds, posture, activity levels, or respiration signals including such as respiration rate or tidal volume. In an example, the signal analyzer circuit 210 can be configured to couple to one or more electrodes such as on one or more of the leads 108A-C and the can 112 connected to the IMB 110, or to couple to one or more physiologic sensors to sense one or more physiologic signals. In an example, the signal analyzer circuit 210 can be coupled to a memory circuit and receive the physiologic signals stored in the memory circuit. Examples of physiologic sensors include pressure sensors, flow sensors, impedance sensors, accelerometers, microphone sensors, respiration sensors, temperature sensors, and blood chemical sensors.

The signal analyzer circuit 210 can generate two or more signal metrics from the one or more physiologic signals. The signal metrics can represent a physiologic change in response to, for example, patient's disease progression, change in medication, change in health conditions, or change in posture or activity levels. The signal analyzer circuit 210 can be coupled to one or more physiologic sensors configured to sense the one or more physiologic signals. The physiologic sensors can be implanted inside a patient's body or external to the patient. In an example, the signal analyzer circuit 210 can generate one or more signal metrics from one sensor. For example, the signal analyzer circuit 210 can receive a transthoracic impedance signal from the electrodes on one or more of the implantable leads such as 108A-C and the can 112, and generate a signal metric of direct-current (DC) impedance using the transthoracic impedance signal. In another example, the signal analyzer circuit 210 can receive a heart sound signal from an accelerometer coupled to the IMD 110, and generate two or more heart sounds metrics including, for example, S1 intensity, S2 intensity, S3 intensity, or timing metrics of the S1, S2, or S3 heart sound with reference to a fiducial point such as a P wave, Q wave, or R wave in an electrocardiogram (ECG) or an electrogram (EGM). In an example, the signal analyzer circuit 210 can receive multiple physiologic signals from multiple sensors. For example, the signal analyzer circuit 210 can receive a blood pressure signal from a pressure sensor and generate two or more blood pressure signal metrics which can include systolic blood pressure, diastolic blood pressure, mean arterial pressure, and the timing metrics of these pressure measurements with reference to a fiducial point.

The device parameter adjustment circuit 220, coupled to the signal analyzer circuit 210, can be configured to determine a desired value for a device parameter using the two or more signal metrics provided by the signal analyzer circuit 210. Examples of the device parameter can include parameters used for sensing a physiologic event, providing patient diagnostic information, assessing device operation and functionality, or controlling the generation and delivery of device therapy such as stimulations to the patient. In an example, the device parameter adjustment circuit 220 can be configured to determine a desired value for a relative timing between a first event in a first site of the heart and a second event in a second site of the heart. One example of the relative timing can include an atrial-ventricular delay (AVD) which represents the latency between an intrinsically occurred atrial electrical activation signal (As) and a subsequent ventricular pacing pulse (Vp), or between an atrial pacing pulse (Ap) and the subsequent Vp. Another example of the relative timing can include a left ventricular-right ventricular delay (VVD) which represents the latency between a left ventricular pacing pulse (LVp) and a right ventricular pacing pulse (RVp).

The device parameter adjustment circuit 220 can include one or more of a sensitivity calculator circuit 221, a variability calculator circuit 222, a covariability calculator circuit 223, or an information fusion circuit 225. The sensitivity calculator circuit 221 can be configured to determine the sensitivity of a signal metric in response to stimulation programmed with a perturbation to the device parameter. In an example, stimulation with at least two distinct device parameter values can be delivered to a target site and the single receiver and analysis circuit 210 receives and measures the resultant signal metric values. The sensitivity calculator circuit 221 can determine the sensitivity of the signal metric using the comparison of the resultant signal metric values. In an example of determining a desired atrio-ventricular delay (AVD) to control the cardiac resynchronization therapy (CRT), the signal analyzer circuit 210 receives a heart sound signal and calculate S1 heart sound intensity (hereinafter "S1 intensity") $\|S1\|_1$ when the AVD is set to a first value $AVD_1$ and the S1 intensity $\|S1\|_2$ when the AVD is set to a second value $AVD_2$; and the sensitivity calculator circuit 221 can determine the sensitivity of S1 intensity to the perturbation of the AVD as the difference between $\|S1\|_1$ and $\|S1\|_2$ (i.e., $\|S1\|_1-\|S1\|_2$) or as a relative change of S1 intensity with respect to the change of AVD (i.e., $(\|S1\|_1-\|S1\|_2)/(AVD_1-AVD_2)$). In an example, the sensitivity calculator circuit 221 can use more than two S1 intensity values $\{\|S1\|_i\}$ corresponding to distinct AVD values $\{AVD_i\}$ where i=1, 2, . . . , N, (N>2) and determine the sensitivity of S1 intensity using as a linear or nonlinear combination of the pair-wise difference of S1 intensity values taken from $\{\|S1\|_i\}$ (i.e., $\|S1\|_i-\|S1\|_j$), or a linear or nonlinear combination of the pair-wise relative change of S1 with respect to the respective change of AVD (i.e., $(\|S1\|_i-\|S1\|_j)/(AVD_i-AVD_j)$). In an example, under a particular AVD value, the sensitivity calculator circuit 21 can use a plurality of measurements of the S1 intensity such as taken at different time and determine a representative S1 intensity from the measurements, and use at least the representative S1 intensity to determine the sensitivity of S1 intensity.

The variability calculator circuit 222 can be configured to determine for at least two of the two or more signal metrics a variability in response to stimulation programmed with a specified device parameter. Alternatively, the signal metric variability can be computed during the baseline when no stimulation being delivered. Examples of the variability can include range, inter-quartile range, standard deviation, variance, sample variance, or other first-order, second-order, or higher-order statistics representing the degree of variation. For example, in determining a desired value for the AVD using the S1 intensity, the variability calculator circuit 222 can perform a plurality of measurements of the S1 intensity when the implantable medical device delivers the stimulation to one or more regions of the heart with a predetermined AVD. The variability calculator circuit 222 can determine the variability of the S1 intensity by computing a variance using the plurality of measurements of the S1 intensity.

The covariability calculator circuit 223 can be configured to determine covariability between the two or more signal metrics in response to stimulation with a specified device parameter. Examples of the covariability can include covariance or cross-correlation between any two of the two or more signal metrics, covariance matrix or cross-correlation matrix, sample covariance or sample cross-correlation matrix, and cross-spectrum or coherence as estimated in the frequency domain. The covariability calculator circuit 223 can determine the covariability between signal metrics using a plurality of measurements of at least two of the two or more signal metrics.

The two or more signal metrics used for covariability determination can be from the same physiologic signal. For example, the covariability calculator circuit 223 can determine the covariability between two or more heart sounds metrics, such as S1 intensity, S2 intensity, S3 intensity, or timing metrics of the S1, S2, or S3 heart sound with respect to a fiducial point such as a Q wave in an ECG or an atrial activation event in an EGM. In an example, the covariability calculator circuit 223 can determine the covariability between two or more signal metrics from different physiologic signals such as acquired from different physiologic sensors coupled to the signal analyzer circuit 210.

The information fusion circuit 225 can be configured to determine the desired device parameter value using one or more of the sensitivity for at least two of the two or more signal metrics, the variability for at least two of the two or more signal metrics, and the covariability between at least two of the two or more signal metrics. In an example, the information fusion circuit 225 can be configured to select one or more from a plurality of signal metrics based at least in part on a comparison of the sensitivity, the variability, the covariability, or any combination thereof. In an example, the information fusion circuit 225 can determine a desired value for the device parameter using a combination of device parameter values estimated from two or more of the selected signal metrics. Examples of the information fusion circuit 225 are discussed below, such as with reference of FIGS. 4 and 5.

The stimulation generation circuit 230 can be configured to generate stimulations for stimulating a target site. In an example, the stimulation generation circuit 230 can generate one or more stimulation trains for stimulating one or more regions of a heart which can include a left ventricle, a right ventricle, a left atrium, a right atrium, a pulmonary artery, a septum between the left and right ventricles, or other epicardial or endocardial sites. In an example, the stimulation generation circuit 230 can generate one or more stimulation trains for stimulating one or more of a neural target including, for example, a baroreceptor regions, nerve trunk, or nerve bundles. The stimulation generation circuit 230 can be coupled to one or more of the implantable leads such as 108A-C to deliver the stimulations to the target sites.

The controller circuit 240 can be included with or coupled to the signal analyzer circuit 210, the device parameter adjustment circuit 220, and the stimulation generation circuit 230. In an example, the controller circuit 240 can adjust one or more programmable stimulation parameters when certain condition is met. Examples of the stimulation parameters can include stimulation pulse strength parameters, pulse waveform or morphology, and stimulation scheduling parameters. The stimulation pulse strength parameters can include, for example, a pulse amplitude, pulse width, pulse morphology, inter-pulse interval, pulse duty cycle, or pulse frequency. Pulse morphology can include a square wave, triangle wave, sinusoidal wave, or waves with desired harmonic components to mimic white noise such as indicative of naturally-occurring baroreflex stimulation. The stimulation pulse can be of one of multiphasic waves including biphasic, triphasic, or multiphasic waves. The therapy schedule parameters can include parameters controlling the time and duration of the stimulation pulse train. In an example, the controller circuit 240 can be configured to program the stimulations using the desired device parameter value provided by the device parameter adjustment circuit 220 and schedule the output of the stimulations from the stimulation generation circuit 230.

Figure 3:
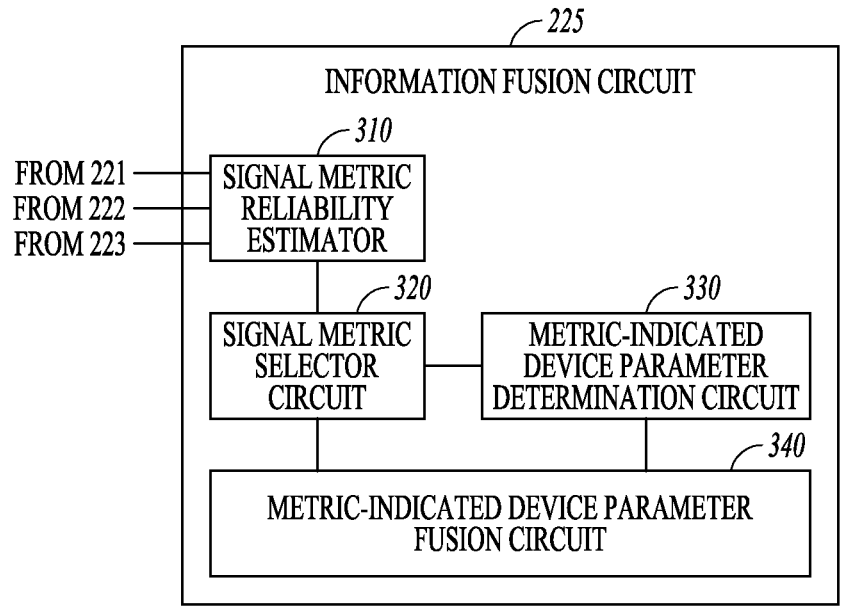
FIG. 3 illustrates an example of an information fusion circuit with signal metric selection.

FIG. 3 illustrates an example of information fusion circuit 225, which can be an example of the information fusion circuit as illustrated in the device parameter adjustment circuit 220. The information fusion circuit 225 can be configured to select one or more signal metrics from a plurality of candidate signal metrics such as those generated by the signal analyzer circuit 210, and determine the desired device parameter using the selected signal metrics.

As illustrated in FIG. 3, the information fusion circuit 225 can include a signal metric reliability estimator circuit 310, a signal metric selector circuit 320, a metric-indicated device parameter determination circuit 330, and a metric-indicated device parameter fusion circuit 340. The signal metric reliability estimator circuit 310 can be configured to compute a signal metric reliability for a signal metric using at least one of the sensitivity such as from the sensitivity calculator circuit 221, the variability such as from the variability calculator circuit 222, or the covariability between the two or more signal metrics such as from the covariability calculator circuit 223. The signal metric reliability can be a quantity representing the responsiveness and consistency of the signal metric in response to the stimulation programmed with a specified device parameter. The signal metric selector 320 can be configured to select a subset from a plurality of candidate signal metrics using a comparison of the signal metric reliability of the signal metrics.

In an example, the signal metric reliability estimator 310 determines the signal metric reliability to be proportional to the signal metric sensitivity, such that a signal metric with a higher sensitivity can be more reliable for use in determining the desired value of the device parameter. For example, the signal metric reliability estimator circuit 310 can be configured to determine for the signal metric a first representative signal metric value $\mu_1$ in response to the stimulation when the device parameter is set to a first value, and a second representative signal metric value $\mu_2$ in response to the stimulation when the device parameter is set to a second value. The representative values $\mu_1$ and $\mu_2$ can be a single measurement under respective device parameter value. The representative values $\mu_1$ and $\mu_2$ can also be determined from a plurality of measurements of the signal metric under respective device parameter value at different time, such as central tendency of the plurality of measurements. Examples of central tendency can include mean, median, weighted-mean, or mode. The signal metric reliability estimator circuit 310 can then determine the signal metric reliability as the distance $d_{12}$ between $\mu_1$ and $\mu_2$, i.e., $d_{12}=|\mu_1-\mu_2|$.

In another example, the signal metric reliability circuit 310 determines the signal metric reliability to be inversely proportional to the signal metric variability, such that a signal metric with a higher variability can be less reliable for use in determining the desired value of the device parameter. The signal metric reliability can also be determined to be proportional to the signal metric sensitivity and inversely proportional to the signal metric variability, such that a signal metric with high sensitivity and low variability can be more likely to be selected for use in determining the desired device parameter. For example, the signal metric reliability estimator circuit 310 can be configured to determine for each signal metric a first representative signal metric value $\mu_1$ in response to the stimulation when the device parameter is set to a first value, and a second representative signal metric value $\mu_2$ in response to the stimulation when the device parameter is set to a second value. The signal metric reliability estimator circuit 310 can further calculate a signal metric variability ($\sigma$) using a plurality of measurements in response to the stimulation when the device parameter is set to a pre-determined value. Alternatively, the signal metric variability ($\sigma$) can be computed during the baseline when no stimulation being delivered. The signal metric reliability estimator circuit 310 can then calculate a sensitivity-to-variability ratio (SVR) using the difference $d_{12}$ and the variability $\sigma$, i.e., SVR=$d_{12}/\sigma$.

The signal metric selector 320 can select the signal metric using the signal metric reliability provided by the signal metric reliability estimator 310. For example, the signal metric selector 320 selects the signal metric if the distance $d_{12}$ meeting a reliability criterion such as die exceeding a reliability threshold, or if the SVR meeting a reliability criterion such as exceeding a reliability threshold.

The metric-indicated device parameter calculator 330 can be configured to determine for each of the selected signal metric a metric-indicated device parameter value. In an example, the metric-indicated device parameter calculator 330 can estimate the metric-indicated device parameter value by interpolating or extrapolating the relationship between the signal metric measurements and the corresponding device parameter values. For example, in determining a desired AVD value, the metric-indicated device parameter calculator 330 can construct the relationship between the measurements of the S1 intensity in response to stimulation when the AVD is set to a number of values. The metric-indicated device parameter calculator 330 can create a regression model between the AVD and the S1 intensity, and estimate the S1 intensity-indicated AVD value using the created model. Examples of the regression model can include linear regression, polynomial regression, power regression, logistic regression, and other parametric and non-parametric models.

The metric-indicated device parameter fusion circuit 340 can be configured to determine a desired value for the device parameter using a combination of a subset or all of the metric-indicated device parameter values of the selected signal metrics. In an example, the metric-indicated device parameter fusion circuit 340 can determine the desired device parameter as the mean, or median, or mode of the metric-indicated device parameter values of the selected signal metrics. In an example, the desired device parameter can be a linear combination of the metric-indicated device parameter values of the subset of the selected signal metrics. In forming the linear combination, each metric-indicated device parameter value can be weighted by the corresponding signal metric reliability. The weight to each metric-indicated device parameter value can also be determined using the population data indicative of relative reliability of the signal metric. In an example, the metric-indicated device parameter fusion circuit 340 can be configured to receive from the system operator an input including a weight assigned to the metric-indicated device parameter value. In an example, the metric-indicated device parameter fusion circuit 340 can determine the desired device parameter value using nonlinear combinations of the metric-indicated device parameter values of the selected signal metrics. Examples of the nonlinear combination can include a decision tree, a neural network, a non-linear combination, or a multivariate regression model.

Figure 4:
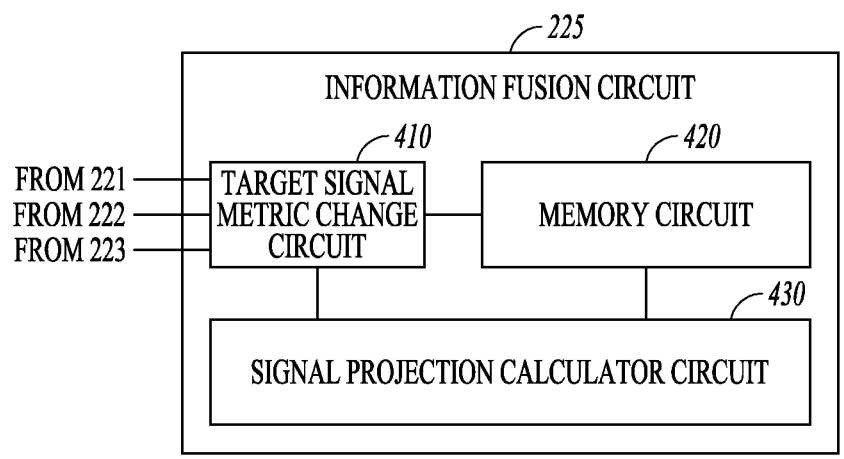
FIG. 4 illustrates an example of an information fusion circuit with signal metric projection.

FIG. 4 illustrates another example of the information fusion circuit 225, which can be an example of the information fusion circuit as a part of the device parameter adjustment circuit 220. The information fusion circuit 225 comprises a target signal metric change circuit 410, a memory circuit 420, and a signal projection calculator circuit 430.

The target signal metric change circuit 410 can be configured to generate a target directional vector representing cumulative change of the two or more signal metrics in response to the stimulation when the device parameter is changed from a first value to a second value. The target directional vector can be generated using at least one of the sensitivity of the two or more signal metrics such as provided by the sensitivity calculator circuit 221, the variability of the two or more signal metrics such as provide by the variability circuit 222, or the covariability between the two or more signal metrics such as provided by the covariability circuit 223. In an example, the target signal metric change circuit 410 can generate the target directional vector (v) using a joint sensitivity computed from two or more signal metrics in response to the stimulation when the device parameter is changed from a first non-optimal value to a second sub-optimal value. The sub-optimal value can be chosen from the historical data such as therapy efficacy on the patient. In another example, the target signal metric change circuit 410 can generate the target directional vector (v) using the joint sensitivity computed from the two or more signal metrics and the covariability between at least two of the two or more signal metrics such as a sample covariance matrix. The target signal metric change circuit 410 can further determine a unit target directional vector $v_0 = v/\|v\|$ where $\|v\|$ denotes the magnitude of v.

The memory circuit 420 can store a plurality of values for the device parameter, from which a desired value can be selected. The signal projection calculator circuit 430, coupled to the memory circuit 420 and the target signal metric change circuit 410, can be configured to receive one stored value for the device parameter at a time and measure the signal metrics in response to a stimulation programmed according to the received device parameter. For example, in determining a desired AVD value, the signal projection calculator circuit 430 can generate a signal metric vector $(X_k)$ that can include the measurements from a total of M signal metrics in response to stimulation programmed with AVD value $(AVD_k)$ taken from the memory circuit 420. The signal projection calculator circuit 430 can compute a projection $(\Omega_k)$ of the signal metric vector $(X_k)$ onto the target directional vector (v) or the unit target directional vector $(v_0)$. In an example, the projection can be computed as a dot product between $X_k$ and $v_0$, i.e., $\Omega_k = v_0^T X_k$. The signal projection calculator circuit 430 can sweep through the stored values of the device parameter and determine the desired device parameter based on the comparison of the resultant projections $\{\Omega_k\}$. In an example, the signal projection calculator circuit 430 determines the desired AVD as the one resulting in the largest projection $\Omega_{max}$.

In another example, the signal projection calculator circuit 430 can be configured to adaptively determine a desired device parameter value. For example, the signal projection calculator circuit 430 can start with an initial value $AV_0$ and determine the resultant projection $\Omega_0$ associated with the measurements of the signal metrics. The signal projection calculator circuit 430 can increase the AVD (i.e., $AVD_0+\Delta$) or decrease the AVD (i.e., $AVD_0-\Delta$) by a step size $\Delta$, and determine the resultant projection $\Omega_1$. The signal projection calculator circuit 430 can compare $\Omega_1$ to $\Omega_0$, and adjust the AVD based on the comparison. For example, AVD can be decremented if $\Omega$ increases from the previous value ($\Omega_1>\Omega_0$), and incremented if $\Omega$ decreases from the previous value ($\Omega_1<\Omega_0$). The process can be continued until the resultant projection $\Omega$ meets a convergence criterion (such as the difference between the present and the previous projections falls below a specified threshold value), where the corresponding AVD value can be determined to be the desired AVT value.

Figure 5:
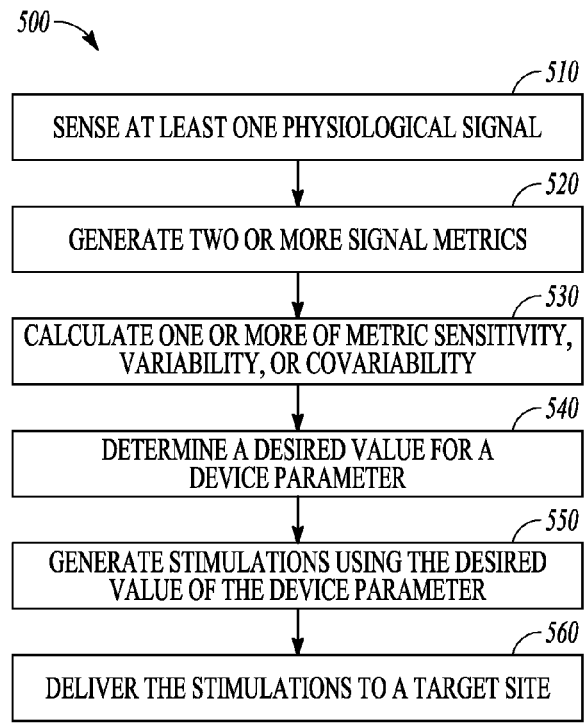
FIG. 5 illustrates an example of a method for determining a desired device parameter and stimulating a target site according to the desired device parameter.

FIG. 5 illustrates an example of a method 500 for determining a desired device parameter and stimulating a target site according to the desired device parameter. In an example, the IMD 110, including its various examples discussed in this document, is programmed to perform method 500, including its various examples discussed in this document.

In an example, the method 500 can be used to determine a desired value for a relative timing between a first event in a first site of the heart and a second event in a second site of the heart. One example of the relative timing between the first and the second events can include an atrial-ventricular delay (AVD) which represents the latency between an intrinsically occurred atrial electrical activation signal (As) and a subsequent ventricular pacing pulse (Vp), or between an atrial pacing pulse (Ap) and the subsequent Vp. Another example of the relative timing can include a left ventricular-right ventricular delay (VVD) which represents the latency between a left ventricular pacing pulse (LVp) and the subsequent right ventricular pacing pulse (RVp). The desired value of the AVD or the VVD can then be used to program one or more stimulation trains to be delivered to one or more of the regions in the heart, such as right atrium (RA), left atrium (LA), right ventricle (RV), or left ventricle (LV), so as to restore the synchronization among various sites of the heart.

One or more physiologic signals can be sensed at 510. Examples of the physiologic signal can include one or more of intrathoracic impedance, intracardiac impedance, arterial pressure, pulmonary artery pressure, RV pressure, LV coronary pressure, coronary blood temperature, blood oxygen saturation, one or more heart sounds, physical activity or exertion level, posture, respiration, body weight, or body temperature. The physiologic signals can be acquired by one or more physiologic sensors including, for example, pressure sensors, flow sensors, impedance sensors, accelerometers, microphone sensors, respiration sensors, temperature sensors, and blood chemical sensors. The physiologic sensors can be implanted inside a patient's body or external to the patient. From the physiologic signals two or more signal metrics can be generated at 520. In an example, the physiologic signal can be a heart sound signal, and the heart sound metrics can include S1 intensity, S2 intensity, S3 intensity, or timing metrics of the S1, S2, or S3 heart sound with respect to a fiducial point such as a P wave or R wave on a ECG or an EGM. The signal metrics can be obtained from two or more physiologic signals sensed by different physiologic sensors.

At 530, one or more of a sensitivity for a signal metric, a variability for a signal metric, or a covariability among two or more signal metrics can be calculated. In an example, the sensitivity can include difference of the signal metric values in response to stimulation with the device parameter programmed to at least two different values. For example, the sensitivity of S1 intensity can be determined as the difference between the S1 intensity $\|S1\|_1$ when the AVD is set to a first value $AVD_1$ and the S1 intensity $\|S1\|_2$ when the AVD is set to a second value $AVD_2$.

The variability can include a spreadness measure computed from a plurality of measurements of the signal metric in response to stimulation with a specified device parameter. In an example, the variability can be computed during the baseline when no stimulation is delivered. Examples of the variability can include range, inter-quartile range, standard deviation, variance, sample variance, or other first-order, second-order, or higher-order statistics representing the degree of variation.

The covariability can include, for example, cross-correlation, covariance, covariance matrix or sample covariance matrix, cross-entropy, and mutual information computed using measurements from two or more signal metrics. The covariability can also include cross-spectrum and coherence as computed in the frequency domain. The two or more signal metrics used for covariability determination can be extracted from the same physiologic signal. For example, the signal metrics can include one or more heart sounds metrics extracted from a heart sound signal, such as the S1 intensity, S2 intensity, S3 intensity, or timing metrics of the S1, S2, or S3 heart sound with respect to a fiducial point. In an example of determining a desired AVD value, during the stimulation of one or more regions of the heart with a predetermined AVD, N (N≥2) measurements for a total of M (M≥2) signal metrics can be obtained. Let the n-th measurement of M signal metrics be denoted by a measurement vector $X_n=[x_{1n}, x_{2n}, \ldots, x_{Mn}]^T$, where $x_{mn}$ denotes the n-th measurement of the signal metric m (1≤m≤M, and 1≤n≤N), and "T" denotes transpose operation of a vector or a matrix. Then, all N measurements for all M signal metrics can be represented by an M-by-N measurement matrix $X_{MN}=[X_1, X_2, \ldots, X_N]$. Let the mean of the N measurement for the signal metric m be denoted by $\mu_m$ and the mean of all M signal metrics be denoted by the mean vector $\mu=[\mu_1, \mu_2, \ldots \mu_M]^T$, then the M-by-M sample covariance matrix $C_{xx}$ representing multivariate variability can be computed as given in equation (1):

$$C_{xx} = \frac{1}{N-1}\sum_{n=1}^{N} (X_n - \mu) * (X_n - \mu)^T \quad (1)$$

At 540, a desired value for the device parameter can be computed using, for example, one or more of the signal metric sensitivity, the variability, or the covariability. In an example, one or more signal metrics from a plurality of candidate signal metrics can be selected based on one or more of the signal metric sensitivity, the variability, or the covariability. The desired value for the device parameter can be computed using an information fusion method such as a linear or nonlinear combination of the signal-metric indicated device parameter values. Examples of the information fusion are discussed below, such as with reference of FIGS. 6 and 7.

On or more stimulation pulse trains can then be generated at 550 using the desired value of the device parameter, and delivered to a target site at 560 to achieved, for example, desired treatment. In an example, the stimulation pulse trains can be delivered to one or more regions of a heart including, for example, a left ventricle, a right ventricle, a left atrium, a right atrium, a pulmonary artery, a septum between the left and right ventricles, and other epicardial or endocardial sites. The stimulation pulse trains can also be delivered to a neural target including, for example, a baroreceptor regions, nerve trunk, and nerve bundles.

Figure 6:
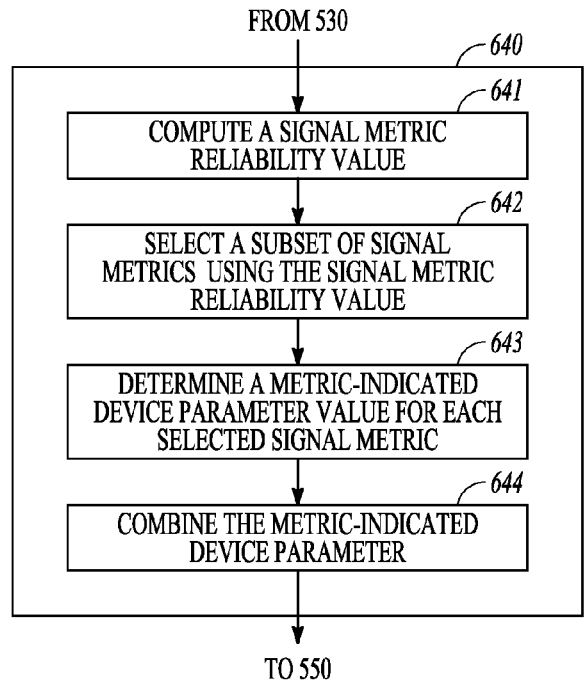
FIG. 6 illustrates an example of a method for determining a desired value for a device parameter using a combination of signal metrics.

FIG. 6 illustrates an example of a method 640 for determining a desired value for a device parameter. The method 640 can be an example of 540. The method starts at 641 by computing a signal metric reliability (XR) for each of the candidate signal metrics. The signal metric reliability can be computed using one or more of the signal metric sensitivity, the variability, or the covariability provided at 530. In an example, the signal metric reliability can be proportional to the signal metric sensitivity. For example, in determining the reliability for a signal metric X, one or more measurements $\{X\}_1$ can be generated in response to the stimulation when the device parameter is set to a first value ($P_1$); and one or more measurements $\{X\}_2$ can be generated in response to the stimulation when the device parameter is set to a second value ($P_2$). A representative value $\mu_1$ can be computed from the measurements $\{X\}_1$ and a representative value $\mu_2$ from the measurements $\{X\}_2$. The representative value $\mu_1$ and $\mu_2$ can be computed as mean, median, weighted-mean, mode, or other central tendency of respective measurements. The signal metric reliability (XR) can be proportional to a distance $d_{12}$ between $\{X\}_1$ and $\{X\}_2$, i.e., $XR=\alpha \cdot |\mu_1-\mu_2|$ where $\alpha$ is a scalar constant.

In another example, the signal metric reliability can be inversely proportional to the signal metric variability, such that a signal metric with a higher variability is less reliable for use in determining the desired value of the device parameter. The variability measure ($\sigma$) can be computed using a plurality of measurements of the signal metric in response to the stimulation when the device parameter is set to a pre-determined value. In an example, the variability measure can be computed using the measurements $\{X\}_1$, $\{X\}_2$, or measurements during the baseline when no stimulation is delivered. Examples of the variability can include range, inter-quartile range, standard deviation, variance, sample variance, or other first-order, second-order, or higher-order statistics representing the degree of variation. The signal metric reliability (XR) can be proportional to the distance $d_{12}$ between $\mu_1$ and $\mu_2$ and inverse proportional to $\sigma$. For example XR can be proportional to a sensitivity-to-variability ratio, i.e., $XR=\alpha \cdot |\|_1-\mu_2|/\sigma$, where $\alpha$ can be a scalar constant.

At 642, a signal metrics can be selected if the signal metric reliability meets a specified criterion. For example, a signal metric can be selected if the distance $d_{12}$ exceeds a reliability threshold, or if the SVR exceeds a reliability threshold.

At 643, for each selected signal metric a metric-indicated device parameter value can be determined. In an example, the metric-indicated device parameter value can be determined using an extrapolation or interpolation of the relationship between the signal metric measurements and the corresponding device parameter values. For example, in determining the desired AVD value, an S1 intensity-AVD relationship can be constructed between the measurements of the S1 intensity in response to stimulation when the AVD is set to a number of values. The relationship can be represented by a regression model. Examples of the regression model can include linear regression, polynomial regression, power regression, logistic regression, and other parametric and non-parametric models. The S1 intensity-indicated AVD can then be determined using the extrapolation or interpolation using the regression model between the S1 intensity and the AVD values.

The desired device parameter value can then be determined at 644 by combining the signal metric-indicated device parameter value of a subset or all of the selected signal metrics. In an example, the combination can include a linear combination of the metric-indicated device parameter values of the subset of the selected signal metrics. Each metric-indicated device parameter value can be weighted by the signal metric reliability associated with the respective selected signal metric. In an example, the combination can include a nonlinear combination of the metric-indicated device parameter value of the subset of the selected signal metrics, such as a decision tree, a neural network, a non-linear combination, or a multivariate regression model. The desired device parameter value can be used to generate stimulations at 550.

Figure 7:
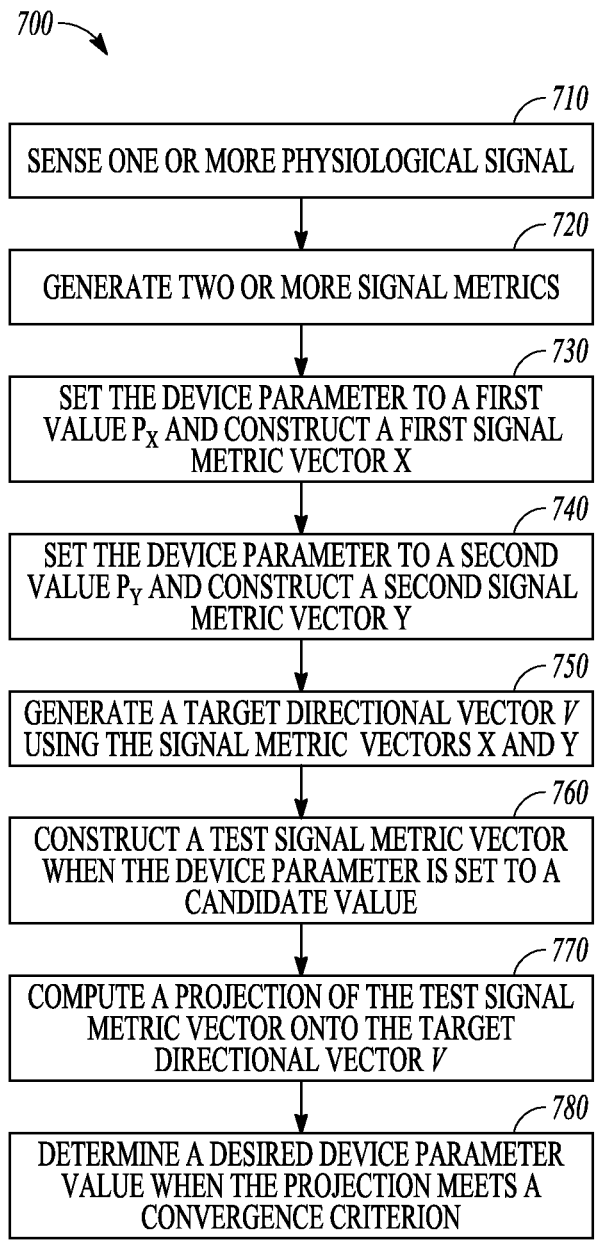
FIG. 7 illustrates an example of a method for determining a desired value for a device parameter using signal metric projection.

FIG. 7 illustrates an example of a method 700 for determining a desired value for a device parameter. In an example, the IMD 110, including its various embodiments discussed in this document, is programmed to perform method 700, including its various embodiments discussed in this document.

One or more physiologic signals are sensed at 710. The physiologic signals can be acquired by one or more physiologic sensors including, for example, pressure sensors, flow sensors, impedance sensors, accelerometers, microphone sensors, respiration sensors, temperature sensors, and blood chemical sensors. From the physiologic signals, two or more signal metrics can be generated at 720. In an example, signal metrics can include features representing a statistical or a morphological characteristic of the physiologic signal. The features can be extracted in time-domain, frequency-domain, or joint time-frequency domain. At 730, by setting the device parameter value to a first value ($P_X$), a first signal metric vector X can be constructed. For example, X can include measurements of the two or more signal metrics in response to stimulation when the device parameter is set to $P_X$. At 740, by setting the device parameter value to a second value ($P_Y$), a second signal metric vector Y can be constructed. The signal metric Y can include measurements of the two or more signal metrics in response to the stimulation when the device parameter is set to the value $P_Y$.

At 750, a target directional vector v can be generated using the signal metric vectors X and Y. The target directional vector can be generated using one or more of the sensitivity of the two or more signal metrics, the variability of the two or more signal metrics, or the covariability between the two or more signal metrics. In an example, the target directional vector can be computed using a joint sensitivity computed from the two or more signal metrics. In an example of determining a desired AVD value, the first signal metric vector $X=[x_1, x_2, \ldots, x_M]^T$ can be generated using the measurements from a total of M signal metrics in response to stimulation to one or more regions of the heart when the AVD is programmed to a first value $AVD_X$; and the second signal metric vector $Y=[y_1, y_2, \ldots, y_M]^T$ can be generated using the measurements from the M signal metrics in response to stimulation when the AVD is programmed to a second value $AVD_Y$. In an example, the first value $AVD_X$ can be arbitrarily selected, so that $AVD_X$ can be less likely to be a desired AVD value; and the second value $AVD_Y$ can be chosen as a sub-optimal AVD value determined based on, for example, therapy history, prior AVD adjustment, or using external information. The target signal metric change circuit 410 can determine the target directional vector (v) in the M-dimensional space as the vector from X to Y, i.e., v=Y−X. A unit target directional vector $v_0$ can be created as $v_0=v/\|v\|$ where $\|v\|$ represents the magnitude of vector v.

In another example, the target directional vector can be determined using the joint sensitivity computed from the two or more signal metrics and the covariability between two or more signal metrics. For example, the signal metric vector X can be repeatedly sampled for N times when AVD is set to $AVD_X$, resulting in an M-by-N measurement matrix $X_{MN}=[X_1, X_2, \ldots, X_N]$ representing the N repeated measurements of the M signal metrics in response of stimulation with $AVD_X$. Similarly, the signal metric vector Y can be repeatedly sampled for N times when AVD is set to $AVD_Y$, resulting in an M-by-N measurement matrix $Y_{MN}=[Y_1, Y_2, \ldots, Y_N]$ representing the N repeated measurements of the M signal metrics in response of stimulation with $AVD_Y$. A representative M-dimensional vector $\mu_X$ can be computed using $X_{MN}$, and a representative M-dimensional vector $\mu_Y$ can be computed using $Y_{MN}$. For example, $\mu_X$ and $\mu_Y$ can be computed as the mean of N measurements $X_{MN}=[X_1, X_2, \ldots, X_N]$ and the mean of N measurements $Y_{MN}=[Y_1, Y_2, \ldots, Y_N]$, respectively. A covariance matrix C can be generated using either $X_{MN}$ or $Y_{MN}$ or any combination of the repeated measurement of X and Y. The M-by-M covariance matrix C represents multivariate variability. In the M-dimensional signal metrics space, the M sensor readings at any given AVD can form an ellipse represented by covariance matrix C. For example, C can be computed using the N repeated measurement of M signal metrics X, as given in equation (2):

$$C = \frac{1}{N-1}\sum_{n=1}^{N}(X_n-\mu_X)*(X_n-\mu_X)^T$$

The target directional vector can then be determined using one or more of $\mu_X$, $\mu_Y$, or C. For example, the target directional vector v in the M-dimensional space can be computed as: $v=C^{-1}(\mu_Y-\mu_X)$. The target directional vector v implicitly accounts for the sensitivity and the variability of the multiple signal metrics. A unit target directional vector $v_0$ can be created as $v_0=v/\|v\|$.

At 760, a test signal metric vector can be constructed. The test signal metric vector can comprise measurements from the two or more signal metrics in response to the stimulation when the device parameter is set to a specified value. In an example, a plurality of candidate device parameter values can be stored in a memory, and the test signal metric vector can be constructed in response to the stimulation when the device parameter is set to one of the candidate device parameter values. Then at 770, a projection of the test signal metric vector onto the target directional vector v can be computed. In an example, the projection can be computed as a dot product between the test signal metric vector and the unit target directional vector $v_0$. The projection can then be compared to a convergence criterion at 780. The candidate device parameter can be deemed the desired parameter value if the projection meets the convergence criterion. Otherwise, a different candidate device parameter value can be selected from the memory, and the resultant test signal metric vector can be projected to the unit target directional vector $v_0$. In an example, the method 700 sweeps through the candidate device parameter values in the memory and determines the desired device parameter as the one that maximizes the projection onto the unit target directional vector $v_0$.

Figure 8:
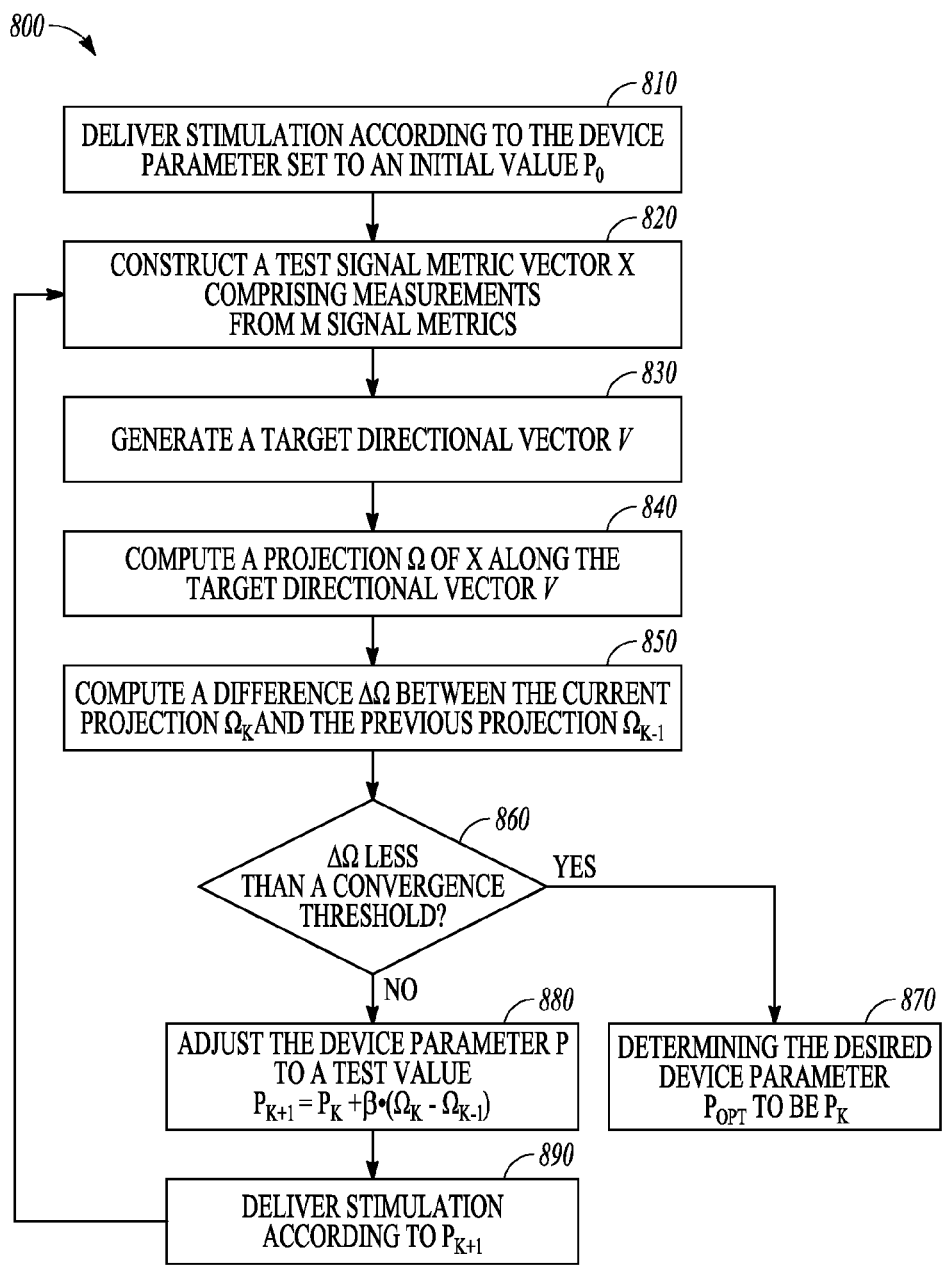
FIG. 8 illustrates an example of a method for adaptively determining a desired value for a device parameter.

FIG. 8 illustrates an example of a method 800 for adaptively determining a desired value for a device parameter. In an example, the IMD 110, including its various embodiments discussed in this document, can be programmed to perform method 800, including its various embodiments discussed in this document.

The device parameter can be initialized to $P_0$ at 810 and the stimulation can be delivered to a target site in accordance with the initial value of the device parameter. The initial value of the device parameter can be chosen using empirical knowledge such as the historical performance of the stimulation therapy. At 820, a test signal metric vector $X_k$ (which corresponds to the device parameter value $P_k$) including measurements from M (M≥2) signal metrics can be constructed. At 830, a target directional vector v can be generated, such as by using the joint signal metric sensitivity alone or in conjunction with the covariability among the M signal metrics, as discussed in 740. The test signal metric vector $X_k$ can be projected onto the target directional vector v (or the unit target directional vector $v_0$) at 840. In an example, the resultant projection $\Omega_k$ can be computed as dot product between the test signal metric vector X and the unit target directional vector $v_0$, i.e., $\Omega_k=v_0^T X_k$. If the previous projection $\Omega_{k-1}$ (which corresponds to a previous device parameter value $P_{k-1}$) is available, a difference ($\Delta\Omega$) between the current projection $\Omega_k$ and the previous projection $\Omega_{k-1}$, defined as $\Delta\Omega=|\Omega_k-\Omega_{k-1}|$, can be computed at 850. The $\Delta\Omega$ can then be compared to a convergence threshold at 860. If $\Delta\Omega$ falls below the convergence threshold, then $\Omega_k$ can be considered converged, and the present device parameter value $P_k$ is deemed the desired value $P_{opt}$. Otherwise, the device parameter can be adjusted from $P_k$ to the next value $P_{k+1}$. In an example, the update can be determined by equation (3):

$$P_{k+1}=P_k-\oplus\cdot(\Omega_k-\Omega_{k-1}) \quad (3)$$

where β can be a positive scalar representing an adaptation rate. According to equation (3), the increment or decrement of device parameter value P can be proportional to the comparison of $\Omega_k$ and $\Omega_{k-1}$. For example, if $\Delta\Omega$ exceeds a convergence threshold and if $\Omega_k>\Omega_{k-1}$, which suggests that the projection increases as the device parameter changes from $P_{k-1}$ to $P_k$, then at 880, $P_{k+1}$ can be decremented. If, however, $\Delta\Omega$ exceeds a convergence threshold and if $\Omega_k<\Omega_{k-1}$, which suggests that the projection decreases as the device parameter changes from $P_{k-1}$ to $P_k$, then at 880, $P_{k+1}$ can be incremented. For example, in determining the desired AVD value, AVD can be initialized to $AVD_0$ which is comparable to the patient's intrinsic P wave to R wave interval. If at k-th iteration, the projection $\Omega$ increases from the previous value ($\Omega_k>\Omega_{k-1}$) and $\Delta\Omega_k=|\Omega_k-\Omega_{k-1}|$ exceeds a convergence threshold, then at the next iteration, $AVD_{k+1}$ can be decremented, i.e., $AVD_{k+1}=AVD_k-\beta\cdot\Delta\omega_k$. Because the update of AVD can be proportional to $\Delta\Omega$, as the $\Omega_k$ gets closer to $\Omega_{k-1}$, the AVD gets fine-tuned to avoid missing the desired AVD due to a too large increment or decrement. The adjusted device parameter $P_{k+1}$ can then be used in generating stimulation and deliver the stimulation to the target site at 890, and a new a test signal metric vector can be generated at 820.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system, comprising:
   a signal sensor circuit coupled to one or more physiologic sensors, the signal sensor circuit configured to sense one or more physiological signals and generate two or more signal metrics from the one or more physiologic signals;
   a stimulator circuit configured to generate and deliver electrostimulation to a heart;
   a controller circuit coupled to the signal sensor circuit and the stimulator circuit, the controller circuit configured to:
      program the stimulator circuit to generate and deliver electrostimulation according to a device parameter programmed to a specified value;
      configure the signal sensor circuit to sense the one or more physiological signals during the electrostimulation and generate the two or more signal metrics; and
      determine a desired value of the device parameter using one or more of respective sensitivity of the two or more signal metrics, respective variability of the two or more signal metrics, or a covariability between the two or more signal metrics, wherein the sensitivity of a respective signal metric is determined using a comparison of values of the same signal metric during stimulation sessions according to the device parameter programmed to different values.

2. The system of claim 1, wherein the controller circuit is configured to program the stimulator circuit with the desired value of the device parameter, and the stimulator circuit is configured to generate and deliver electrostimulation according to the device parameter with the desired value.

3. The system of claim 1, comprising one or more medical devices including an implantable medical device, a subcutaneously implanted device, or a wearable external device, wherein the one or more physiological sensors are coupled to the one or more medical devices.

4. The system of claim 1, wherein the device parameter includes an atrial-ventricular delay indicative of a time delay between an atrial activation and an onset of ventricular stimulation.

5. The system of claim 1, wherein the device parameter includes a ventricular-ventricular delay indicative of a time delay between an onset of left-ventricular stimulation and an onset of right-ventricular stimulation.

6. The system of claim 1, wherein the stimulator circuit is configured to generate and deliver electrostimulation at one or more sites of the heart according to the device parameter programmed to a specified value.

7. The system of claim 6, wherein the stimulator circuit is configured to generate and deliver electrostimulation at two or more sites of a left ventricle of the heart.

8. The system of claim 6, wherein the stimulator circuit is configured to generate and deliver a cardiac resynchronization therapy including synchronized electrostimulation at a first site of a left ventricle of the heart and a second site of a right ventricle of the heart.

9. The system of claim 1, wherein the one or more physiological sensors include one or more of a thoracic impedance sensor, a heart sound sensor, a blood pressure sensor, a respiration sensor, or a posture or activity sensor.

10. The system of claim 1, wherein the control circuit is configured to determine the variability including a variance or a standard deviation of one of the two or more signal metrics, and to determine the covariability including a correlation or a covariance between two of the two or more signal metrics.

11. The system of claim 1, wherein the control circuit is further configured to:
select a subset of the two or more signal metrics based on a comparison between respective signal metric reliability of the two or more signal metrics, the signal metric reliability being proportional to the signal metric sensitivity and inversely proportional to the signal metric variability; and
determine the desired value of the device parameter based on responses of the signal metrics of the selected subset to the electrostimulation according to the device parameter programmed to a specified value.

12. The system of claim 1, wherein the control circuit is configured to adaptively determine the desired value of the device parameter when a projection of a signal metric vector onto a target directional vector satisfies a convergence criterion;
wherein the signal metric vector includes measurements from the two or more signal metrics; and
wherein the target directional vector is determined using the respective sensitivity of the two or more signal metrics and the covariability between the two or more signal metrics.

13. A method for operating a medical system to treat a cardiac disease in a patient, the method comprising:
generating and delivering electrostimulation to a heart of the patient using an eletrostimulator according to a device parameter having a specified value;
sensing one or more physiological signals during the electrostimulation using one or more physiologic sensors;
generating from the one or more physiological signals two or more signal metrics; and
determining a desired value of the device parameter using one or more of respective sensitivity of the two or more signal metrics, respective variability of the two or more signal metrics, or a covariability between the two or more signal metrics, wherein the sensitivity of a respective signal metric is determined using a comparison of values of the same signal metric during stimulation sessions according to the device parameter programmed to different values.

14. The method of claim 13, further comprising:
programming the stimulator circuit with the desired value of the device parameter; and
generating and delivering electrostimulation according to the device parameter programmed to the desired value.

15. The method of claim 14, wherein the electrostimulation is delivered at two or more sites of a left ventricle of the heart.

16. The method of claim 14, wherein the electrostimulation includes a cardiac resynchronization therapy including synchronized electrostimulation at a first site of a left ventricle of the heart and a second site of a right ventricle of the heart.

17. The method of claim 13, wherein sensing one or more physiological signals includes sensing using respective physiological sensors, one or more of a thoracic impedance signal, a heart sound signal, a blood pressure signal, a respiration signal, or a posture or activity signal from the patient.

18. The method of claim 13, wherein the device parameter includes one or more of an atrial-ventricular delay indicative of a time delay between an atrial activation and an onset of ventricular stimulation, or a ventricular-ventricular delay indicative of a time delay between an onset of left-ventricular stimulation and an onset of right-ventricular stimulation.

19. The method of claim 13, further comprising:
selecting a subset of the two or more signal metrics based on a comparison between respective signal metric reliability of the two or more signal metrics, the signal metric reliability being proportional to the signal metric sensitivity and inversely proportional to the signal metric variability; and
determining the desired value of the device parameter based on responses of the signal metrics of the selected subset to the electrostimulation according to the device parameter programmed to a specified value.

20. The method of claim 13, wherein determining a desired value of the device parameter includes:
determining a projection of a signal metric vector onto a target directional vector, the signal metric vector including measurements from the two or more signal metrics, and the target directional vector determined using sensitivity of the two or more signal metrics and the covariability between two or more signal metrics; and
adaptively determining the desired value of the device parameter when the projection satisfies a convergence criterion.

* * * * *